Figure 9:
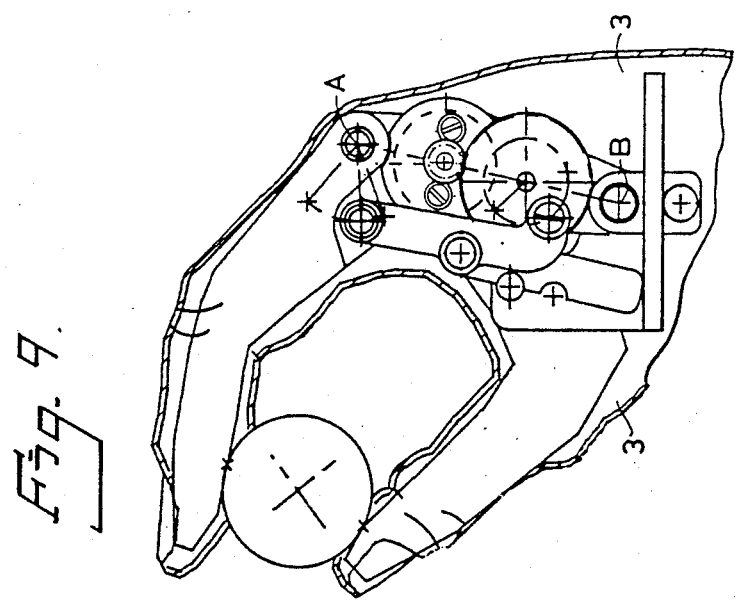

United States Patent [19]

Rennerfelt

[11] Patent Number: 4,792,338
[45] Date of Patent: Dec. 20, 1988

[54] ARTIFICIAL HAND

[75] Inventor: Gustav Rennerfelt, Lidingö, Sweden

[73] Assignee: Centri Gummifabrik AB, Järfäla, Sweden

[21] Appl. No.: 919,046

[22] Filed: Oct. 15, 1986

[30] Foreign Application Priority Data

Oct. 15, 1986 [SE] Sweden ................... 8504780

[51] Int. Cl.⁴ ............................................. A61F 2/54
[52] U.S. Cl. ........................................ 623/64; 623/62; 623/57; 414/4
[58] Field of Search ............ 623/64, 65, 57, 21, 623/24, 25, 63, 62, 61; 414/1, 4

[56] References Cited

U.S. PATENT DOCUMENTS

| 645,740 | 3/1900 | Schenk | 623/63 |
| 1,385,669 | 7/1921 | Dilworth | 623/64 |
| 1,465,933 | 8/1923 | Dedic | 623/63 X |
| 2,230,378 | 2/1941 | Fzberle | 623/64 |
| 2,287,781 | 6/1942 | Carnes | 623/64 X |
| 2,486,746 | 11/1949 | Jinkins | 623/63 |
| 2,553,277 | 5/1951 | Robinson et al. | 623/57 X |
| 3,345,647 | 10/1967 | Gentilvomo | 623/63 X |
| 3,631,542 | 1/1972 | Potter | 623/25 |
| 3,967,321 | 7/1976 | Ryan et al. | 623/24 |
| 3,985,238 | 10/1976 | Nakura et al. | 414/4 X |
| 4,094,016 | 6/1978 | Eroyan | 623/63 X |
| 4,501,522 | 2/1985 | Causer et al. | 414/4 |
| 4,685,928 | 8/1987 | Yaeger | 623/25 X |

FOREIGN PATENT DOCUMENTS

| 0828272 | 5/1938 | France | 623/57 |
| 0764671 | 9/1980 | U.S.S.R. | 623/24 |
| 854388 | 8/1981 | U.S.S.R. | |
| 0895430 | 1/1982 | U.S.S.R. | 623/64 |
| 072020 | 9/1981 | United Kingdom . | |

Primary Examiner—Richard J. Apley
Assistant Examiner—Howard Flaxman
Attorney, Agent, or Firm—Witherspoon & Hargest

[57] ABSTRACT

The invention relates to an artificial hand or prosthesis with a carcase, a palm and a finger pair, a thumb and a link (20). Distinguishing for the invention is that the movement pattern of the thumb in relation to the movement of the finger pair, the pattern being provided by the palm on which the thumb is rigidly attached being pivotably connected to the carcase about a wrist turning point (B) and by the finger pair being connected to the palm via the finger joint turning point (A). A link mechanism comprising four joints (inter alia 29, A, B) controls the gripping movements of the prosthesis, and is driven by an electric motor located in the palm in the preferred embodiment.

6 Claims, 4 Drawing Sheets

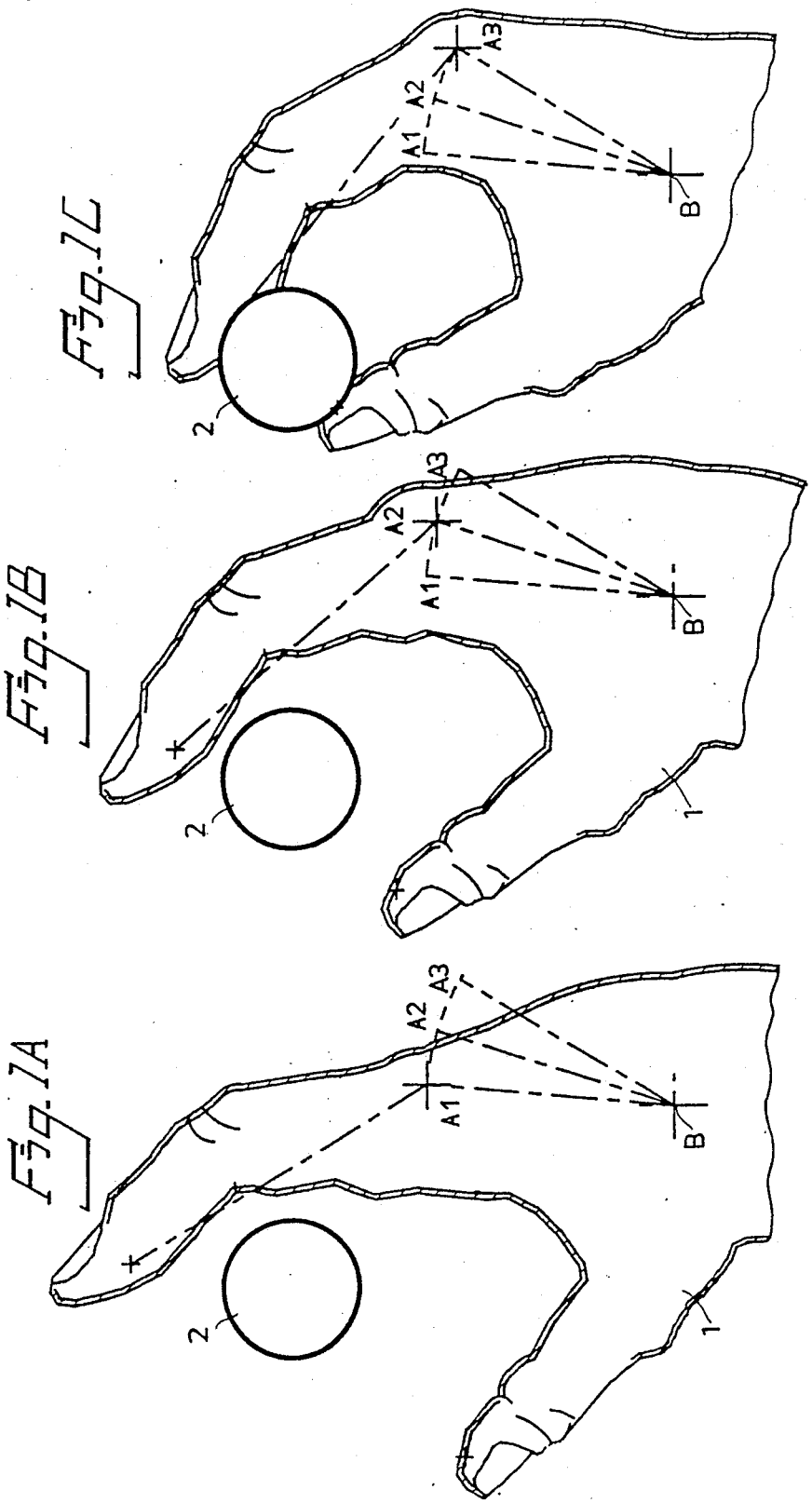

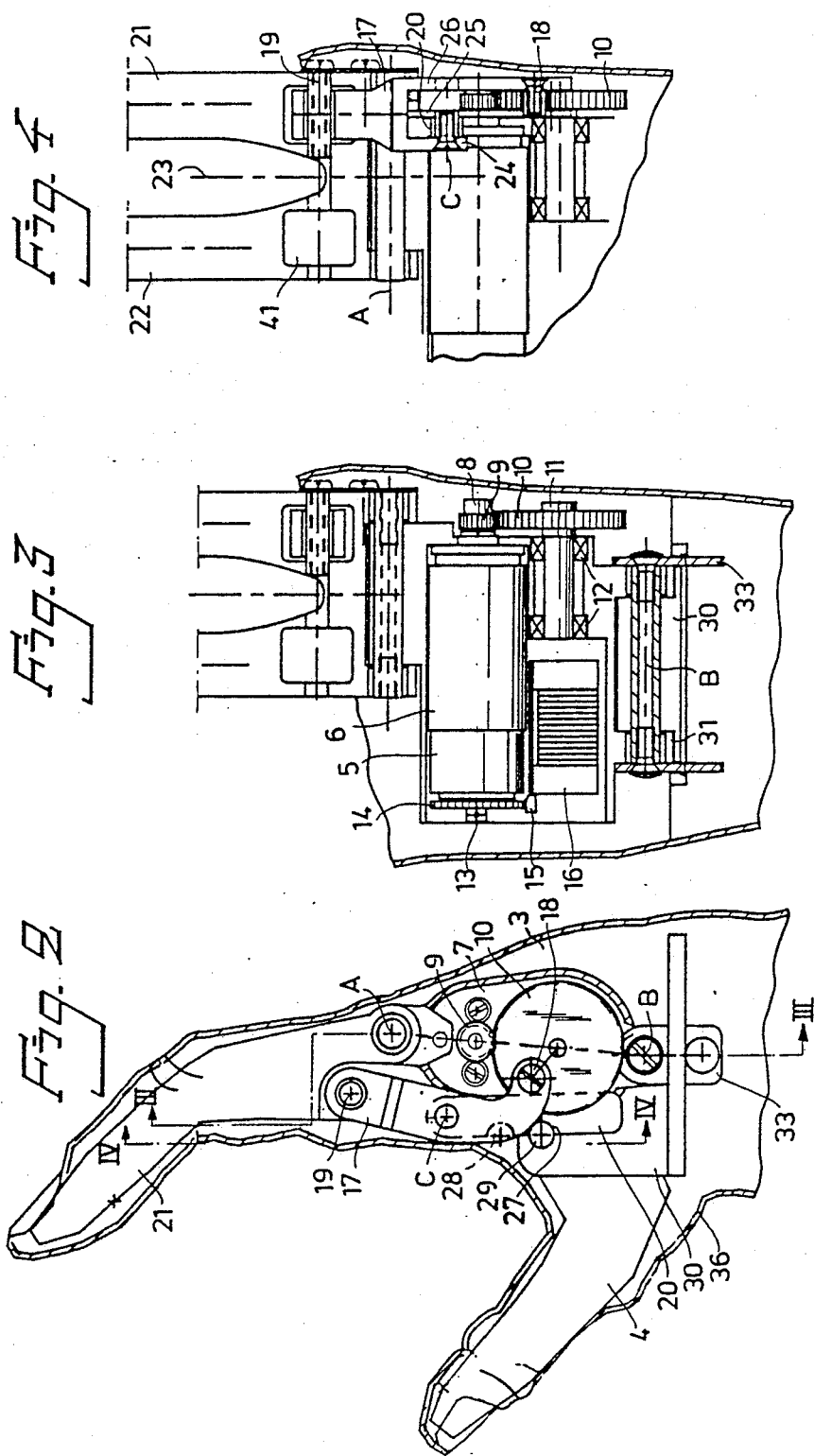

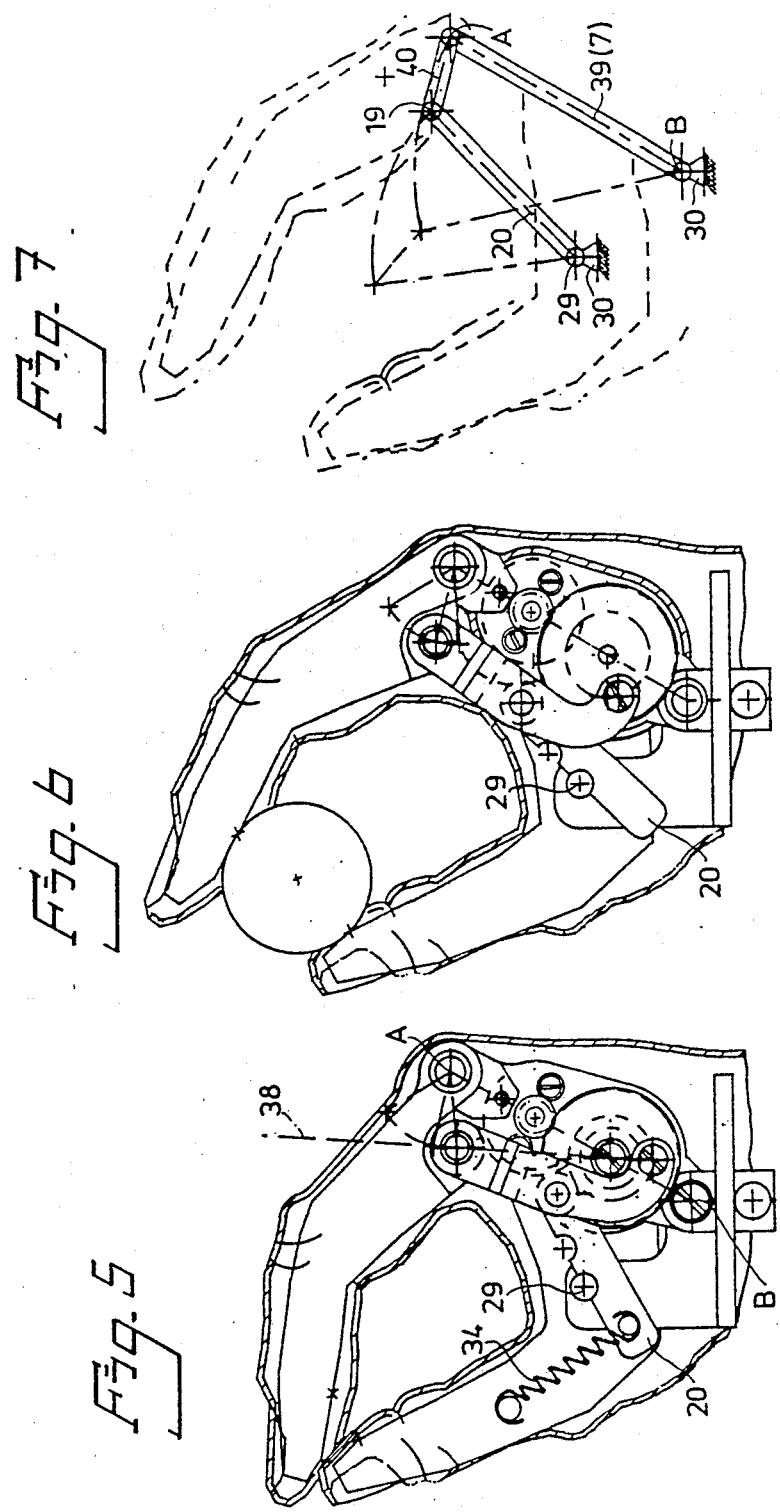

ARTIFICIAL HAND

In an amputation of the hand one strives to keep the length of the remaining forearm as long as possible. A patient requirement is also that the arm provided with the artificial hand or hand prosthesis (hereinafter designated "prosthesis") shall be just as long as the patient's other arm. This leads to the requirement that the prosthesis shall be short, since the compulsion to amputate an extra length of arm to make the arm provided with the prosthesis just as long as the patient's other arm is something to be avoided, of course.

Many other requirements can be made on a prosthesis, apart from the one that it shall be short. The requirement vary, depending on whether the prosthesis is intended for an adult or a child. The desired features of a prosthesis enumerated below are a compromise between reasonable technical properties, cosmetically acceptable instrumentation and a fairly natural pattern of movement.

Of the technical functions there may be mentioned that the prosthesis shall provide a three-point grip, i.e. a grip imitating the one achieved by a natural hand when the thumb, index and long fingers grip an object. This grip shall be powerful, in the order of magnitude 25 N and shall be locked mechanically in all positions. The electric motor driving the fingers shall only consume current when resetting the positions of the fingers, thus to save the battery. The technical requirements also include that the prosthesis shall include means for turning the wrist in a plane at right angles to the forearm.

Included in the cosmetic requirements placed on the prosthesis in accordance with the invention is that it shall imitate a natural hand as far as possible, particularly with regard to the size of the thumb and its placing in relation to the remaining fingers. The prostheses in the art today have a thumb which is unnaturally long in relation to the remaining fingers and which is placed substantially at the centre of the palm.

Included in the requirements placed on the movement pattern of the prosthesis in accordance with the present invention is that an object shall be able to be picked up from a table top while the forearm is substantially parallel with the top. With the prostheses in the art today the entire forearm must be at a considerable angle to the table top before the object can be picked up. This gives an unnatural impression. Another factor contributing to the movement pattern of a prosthesis giving an unnatural impression is the weight of it. The present invention strives to ensure that the weight of the prosthesis does not exceed that of the natural hand. In actual fact the weight of the prosthesis should really be even less than that of a natural hand so that if the stump is short is is not subjected to troublesome loading.

The technical requirements made on the prosthesis in accordance with the invention is that its parts shall easily be able to be removed for service or replacement. In addition, the mechanical structure shall be symmetrical to a great degree, which means that the same structural parts can be used both for right hand and left hand prostheses.

The GB-A No. 072 020 describes a hand prosthesis generally used in Sweden today, which has the disadvantage of being too long, too heavy and with an unnaturally long thumb.

The SU-A No. 854 388 illustrates a prosthesis which is unnaturally long and has a thumb turning about an axis at the second joint of the thumb counted from the tip thereof. Remaining fingers can be turned about a common second axis which is situated at the third joint, counted from the tip of the index finger. Similarly to the British patent, the electric motor is situated in the carcase of the prosthesis, i.e. the structure which is stationary relative the forearm.

The present invention has the object of providing a prosthesis of the kind mentioned above, which avoids the disadvantages of the known prosthesis and has the introductorily mentioned desired properties of being short, cosmetically pleasing and with a natural pattern of movement. These properties are achieved by the prosthesis having the distinguishing features disclosed in claim 1.

A salient feature of the prosthesis in accordance with the invention is that its grip is self-locking (without the aid of any braking device acting on the motor) when the thumb engages against the index finger structure.

Thanks to the unique feature that the wrist can be angled in relation to the forearm, that it can also assume one of preferably two discrete so-called picking positions (angular positions) and that it can also be rotated in a plane at right angles to the longitudinal direction of the forearm, an object may be picked up from a table surface without the elbow needing to be raised from the surface. The wearer of a prosthesis often prefers to keep it in a jacket pocket during walking. Since the inventive prosthesis can be angled relative the forearm a prosthesis thus angled and placed in a jacket pocket gives a natural impression.

Figure 8:
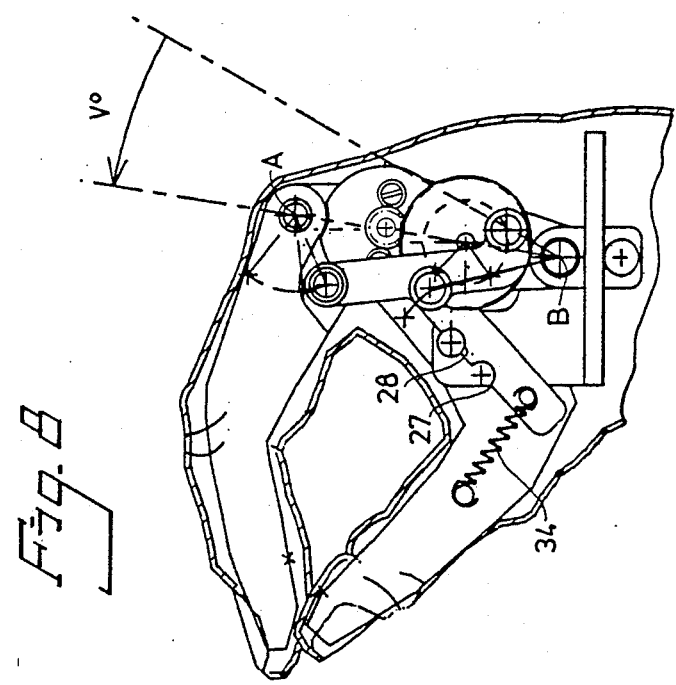

The invention will now be described in detail below in connection with the accompanying drawings, on which FIGS. 1A-C illustrates the movement of the inventive prosthesis when gripping an object, FIG. 2 is a side view of the mechanical structure of the prosthesis, FIG. 3 is a section along the line III—III in FIG. 2, FIG. 4 is a section of the prosthesis along the line IV—IV in FIG. 2, FIGS. 5 and 6 are sections of the prosthesis in its normal attitude towards the forearm, FIG. 7 generally illustrates the link mechanism in the prosthesis in accordance with the invention and FIGS. 8, 9 illustrate the prosthesis in an attitude where the hand is more angled relative the forearm, i.e. the so-called picking attitude of the prosthesis.

FIGS. 1A-C illustrate the movement principle for the prosthesis 1 in accordance with the invention. The index finger structure, comprising a finger pair, is turnable about a finger joint turning point A while the palm, with which the thumb is rigidly connected is turnable round a wrist turning point B. The locations of the turning points A and B and the rigid connection of the thumb with the movable palm causes the gripping movement to imitate the gripping movement of a natural hand. Simultaneously as the index finger is turned anticlockwise round the turning point A this turning point A is turned clockwise round the wrist turning point B from the initial position A1 via the intermediate position A2 to the final position A3.

The object to be gripped, in this case a ring, is denoted by the numeral 2. The large cross inside the object represents the point at which the thumb pressure point, marked by a small cross is to meet the pressure point of the finger pair, similarly marked with a small cross diametrically opposingly across the object. If instead the finger pair were to meet the thumb the finger pressure point will have shifted outwards a distance. With a natural hand, the pressure point of the fingers moves inwards in a direction towards the finger joint when the object to be gripped increases in diameter. This is also applicable to the inventive prosthesis.

The link mechanism steering the movements of the fingers and which is driven by an electric motor, is illustrated in FIGS. 2-4. The motor driven link mechanism is placed in the movable palm 3 with which the thumb 4 is rigidly connected, and which includes an electric motor 5 with a built-in gear 6. The motor is situated close to the finger joint turning point A and is mounted in a housing 7, which together with the surrounding soft structure constitutes the palm 3. On the output shaft 8 of the gear 6 there is a pinion 9 meshing with a main drive gear wheel 10, which in turn is non-rotatably mounted on a shaft 11, which is firmly journaled with the aid of bearings 12 at the side of the motor inside the housing 7. The motor is of the type having a through shaft, which also projects out from the motor housing on the side opposite to the gear. This projecting portion of the shaft is denoted by 13 and on it there is a disk 14 with teeth around its circumference which are intended to engage a pawl arranged on a metal leaf spring which is actuated by an electromagnet 16. Unillustrated batteries feed the motor 5 and electromagnet 16 with current via a similarly unillustrated switch. When the circuit is closed, e.g. by actuation from myoelectrical electrodes known per se and arranged on the forearm, the electromagnet attracts the spring and the pawl 15 is released from its engagement with the disk 14, the motor then turning the main drive gear wheel 10. When the finger pair assumes the desired gripping position, the current is interrupted and the motor poles are shortcircuited, thus causing the motor to stop rapidly with its shaft 13 locked in position by the pawl 15.

An operating link 17, also called the finger link, is pivotably mounted on the main drive gear wheel 10 with the aid of a journaling pin 18, and at its other end it is pivotably mounted on the finger pair by a second journaling pin 19, which is arranged spaced from the turning point A. It is thus obvious that the link 17 transfers the rotational movement of the motor to a turning of the finger pair.

It will be seen from FIGS. 2 and 4 how the link 17, seen from one side in FIG. 2, is substantially straight and has a portion, the end of which terminates in a fork, the legs 25,26 of which (see FIG. 4) are astride the main drive gear wheel 10. A picking link 20 is pivotably connected at one end to the link 17 at a turning point substantially at the centre of the link 17. More specifically, the pivotable connection is arranged with a second fork, formed by the fork leg 25 and a fork leg 24 on the link 17. The picking link 20 is elongate, as seen from the side in FIG. 2, and has a plurality of recesses 27 and 28, two in this case, arranged along one long side of the link. A tension spring 34, for the sake of clarity only illustrated in FIG. 8, maintains (see FIG. 2) the recess 27 (in FIG. 5 the recess 28) in engagement with a projection 29 rigidly attached to a prosthesis carcase 30. From FIG. 3 will be seen that the palm structure, with the housing 7 fixed thereon with the aid of a hinge-like joint 31, is pivotably connected to the carcase 30, the turning pin 32 of the hinge forming said wrist turning point B. The carcase 30 has two upstanding ears 33 with the aid of which the prosthesis is connected, either directly or via some kind of turning joint, to the forearm. It is thus clear that the turning movements of the motor via the link 17 and picking link 20 are transferred into a turning movement of the palm and the thumb 4 fixed on it. The exact location of the turning point of the picking link 20, denoted in FIGS. 2 and 4 by C on the operating link 17, acts on the angular stroke of the wrist turning movements round the turning point B. With the illustrated location, approximately at the centre of the operating link 17, there is obtained the relationship between the wrist and finger pair turning movements illustrated in FIGS. 1A-C.

The finger pair 1 comprises two mutually united fingers 21, 22, as will be seen from FIGS. 3 and 4. The finger 21 represents the index finger, while the finger 22 represents the middle finger.

The self-locking function of the prosthesis grip mentioned in the introduction will now be described with guidance from FIGS. 5-7. In FIG. 5 the main drive gear wheel 10 has turned about 150° anticlockwise from the position in FIG. 2, and the thumb and finger pair engage against each other. Apart from locking of the grip occurring as the result of the torque of the motor 5, the gear 6, pinion 9 and detent means 14,15, the link mechanism is in a self-locking position, since the first turning point 18, the shaft 11 the second turning point 19 are all situated along one line, denoted by the numeral 38 in FIG. 5, whereby forces which can turn the finger pair cannot provide any torque on the link mechanism, which means that the grip cannot be opened. It should be noted that this self-locking of the link mechanism occurs independently of the arm position in space. Thus, self-locking occurs if the prosthesis wearer is walking and carrying a bag between the thumb of the prosthesis and the fingers engaging against the thumb. The same self-locking occurs if the person uses his hands to hang from a pair of Roman rings, for example.

FIG. 7 is referred to for illustrating the movement pattern of the link mechanism, this figure showing a system comprising three links with four articulation points. This link system illustrates the links of the prosthesis in a generalized form where certain simplifications have been made. The link 17 has not been illustrated, and the picking link 20 is assumed to be connected to the turning point 19 on the index finger. The wrist turning point B is fixed to the carcase 30. The numeral 39 denotes the schematically illustrated link, in reality included in the palm, which comprises the housing 7 and the soft structure surrounding the housing. The link 40 is schematically illustrated, and in reality includes the part of the finger pair 21, 22 extending between the finger joint-turning point A and turning point 19 on the finger pair. The picking link is denoted by 20, and thus extends between said end turning point 19 and a fixed projection 29 on the carcase 30. It should be noted that the projection 29 in FIG. 7 is in reality at a higher level than the wrist turning point B. By this arrangement the picking link 20 will be shorter than the link 39. The position of the link system shown with full lines is the initial position, corresponding to the hand attitude in FIG. 5.

From FIG. 7 it will be seen that if the link 20 is shortened by the recess 28 being taken into engagement with the projection 29 the wrist will be turned anti clockwise round the turning point B. In this position, which is illustrated in FIGS. 8 and 9, the prosthesis assumes a so-called picking position. In this position the prosthesis can pick an object e.g. from a table top simultaneously as the forearm is kept substantially parallel to the top. In the illustrated embodiment of the invention, the prosthesis can be moved from the grip position in FIGS. 5 and 6 to the picking position in FIGS. 8 and 9. The picking position is assumed by the wearer manually, e.g. with the fingers of the other hand, turning and moving the link 20 against the bias of the spring 34, until its recess 28 comes into engagement with the projection 29. It is thus obvious that while retaining the normal proportion between the length of the thumb and index finger an object can be picked without needing to angle the forearm an unnatural amount relative to the table top.

A continued opening movement for the fingers from the position illustrated in FIG. 9 results in that the picking link 20 is turned anticlockwise, and normally that the recess 28 moves out from engagement with the projection 29 as well, so that the picking link glides into the position illustrated in FIG. 2 under the action of the spring bias, the prosthesis thus being turned clockwise round the wrist turning point B from the picking position according to FIGS. 8 and 9 to the position in FIG. 2, and from where the prosthesis can be taken to the normal gripping position illustrated in FIGS. 5 and 6 by operation of the motor.

As will be seen from FIGS. 3 and 4, the prosthesis is implemented symmetrically to a great extent, which means that the same details which are used for the illustrated right hand can also be used for a left hand prosthesis. Apart from the thumb, the unsymmetrical details are the operating link 17 and carcase 30. The finger pair 21, 22 is symmetrical about a symmetry line 23, as will be seen from FIG. 4, and thus the operating link 17 will be fitted in to the chamber 41 (illustrated in FIG. 4) for a left hand prosthesis. As will be seen from FIGS. 4 and 6, all the details in the prosthesis are generally easily accessible from a single side, which facilitates service.

Thumb, finger pair 21, 22, palm and carcase are made in light metal, e.g. aluminum, or other stiff material such as reinforced plastics. The link mechanism is protected by an unillustrated casing. Over the entire apparatus is then moulded a conventionally produced replica of the other hand of the wearer in a semi-hard plastics, e.g. foamed polyurethane, and a conventional, exchangeable, cosmetic glove is put on.

The embodiment of the invention described above can be modified in many ways and varied within the scope of the inventive concept. Two different picking positions have been shown. If so desired, the structure may of course be arranged for several picking positions, by providing the picking link 20 with a correspondingly larger number of recesses 27, 28. An infinitely varible setting of the picking position is also possible. Locking the motor shaft can also be arranged by other means than those shown. For example, the disc 14 may be provided with a peripheral frictional surface intended for engagement with a frictional coating on the leaf spring operated by the electromagnet. An alternative embodiment of the motor-braking mechanism is a solenoid, the armature of which is axially displaceable and which acts on the disc 14 by spring bias. A still further alternative is to exchange the disc 14 for a pin passing through the motor shaft and having a detent abutment in its path of movement, this abutment being in turn operated by an electromagnet or a small electric motor. In the illustrated embodiment, one end of the picking link 20 is journalled approximately at the centre of the operating link 17 at C. However, it is possible to locate this turning point C on the link 20 at the turning point 19, or at some other point below this along the operating link 17.

I claim:

1. A hand prosthesis comprising a palm member, index finger means pivotably connected to said palm member for pivoting round a finger turning point, a thumb rigidly attached to said palm member in a position opposing the pivotal movement of the index finger means and having a length and location corresponding to those of a natural hand, and arranged within said palm member,
   - a carcase to which said palm member is pivotably connected round a wrist turning point and adapted to be attached to a forearm,
   - electric motor means provided at said plan member oriented perpendicular to said forearm and being positioned slightly below the juncture of said thumb and said palm, said electric motor means being provided with gear means,
   - a link assembly extending from said wrist turning point to said finger turning point, to a turning point provided on said index finger means spaced from said finger turning point, an additional link and from there back to said carcase,
   - a finger drive link operatively connected between said link assembly and said gear means to move, upon rotation of said electric motor means, said link assembly so as to move said index finger means relative to said thumb in a natural gripping movement pattern such that when said index finger means is rotating round said finger turning point in one direction said finger turning point is concomitantly rotated round said wrist turning point in an opposite direction, and
   - said link assembly comprising said additional link pivotably mounted at one end thereof to said finger drive link and at an opposite end to said carcase round a further turning point spaced from said wrist turning point, whereby said finger drive link is pivotably mounted to said gear means at one end thereof and to said index finger means round a turning point spaced from said finger turning point at its opposite end.

2. A hand prosthesis in accordance with claim 1 wherein said gear means comprises a pinion mounted on an output shaft of said electric motor means, a main drive gear wheel mounted on a shaft journalled for rotation at the side of said electric motor means and meshing said pinion, said finger drive link at said one end thereof being forked, said forked one end straddling said main drive gear wheel and being pivotally mounted at said main drive gear wheel at a gear wheel pivot point with the aid of a journalling pin.

3. A hand prosthesis in accordance with claim 2 wherein in one mode said thumb and said index finger means are self-locked closed against each other when said gear wheel pivot point, said shaft of said maid drive gear wheel, and said turning point of said finger drive link at said index finger means all are aligned.

4. A hand prosthesis in accordance with claim 3, wherein the functional length of said additional link is adjustable for setting attitude of said hand prosthesis relative to said forearm.

5. A hand prosthesis in accordance with claim 4, wherein said additional link is provided with a plurality of recesses at said opposite end for attachment to said further turning point, each of which corresponds to a different attitude of said hand prosthesis relative to said forearm.

6. A hand prosthesis in accordance with claim 5 wherein said one end of said additional link is pivotably mounted generally at the center of said finger drive link.

* * * * *